(12) United States Patent
Ulmer et al.

(10) Patent No.: US 7,005,125 B2
(45) Date of Patent: Feb. 28, 2006

(54) PERSONAL CARE PRODUCTS

(75) Inventors: Herbert Ulmer, Hoboken, NJ (US); Timothy Gillece, Pompton Plains, NJ (US); John Katirgis, West Caldwell, NJ (US)

(73) Assignee: ISP Investments Inc., Wilmington, DE (US)

( * ) Notice: Subject to any disclaimer, the term of this patent is extended or adjusted under 35 U.S.C. 154(b) by 444 days.

(21) Appl. No.: 10/353,390

(22) Filed: Jan. 29, 2003

(65) Prior Publication Data

US 2004/0042987 A1 Mar. 4, 2004

Related U.S. Application Data

(63) Continuation-in-part of application No. 10/233,838, filed on Aug. 30, 2002.

(51) Int. Cl.
*A61K 31/785* (2006.01)
*A61K 31/797* (2006.01)
*A61K 31/77* (2006.01)
*A61K 31/765* (2006.01)
*A61K 31/80* (2006.01)

(52) U.S. Cl. .............................. 424/78.36; 424/78.32; 424/78.33; 424/78.37; 424/78.38

(58) Field of Classification Search ................ 424/400, 424/70.17
See application file for complete search history.

(56) References Cited

U.S. PATENT DOCUMENTS

| 5,994,385 A | * | 11/1999 | Ulmer et al. | ................ 514/397 |
| 6,025,501 A | * | 2/2000 | Ulmer et al. | ................ 548/545 |
| 2004/0042989 A1 | * | 3/2004 | Ulmer et al. | ............ 424/70.11 |

* cited by examiner

*Primary Examiner*—Thurman K. Page
*Assistant Examiner*—David Vanik
(74) *Attorney, Agent, or Firm*—William J. Davis; Walter Katz

(57) ABSTRACT

Personal care products, particularly hair care products, are made herein by mixing (A) a polymer having defined repeat units of a monomer (e.g. α-olefin) maleic anhydride alkyl half-ester or full acid, maleamic acid and maleimide, which is derivatized with an amine, and (B) a compound or polymer having a carboxylic acid functionality. These products exhibit excellent high humidity curl retention properties, as well as an advantageous blend of toughness and cohesiveness, and a strong affinity to natural fibers, when applied to keratin-based fibers, e.g. hair, skin, or textiles, e.g. cotton, wool; and also they are water-soluble and water-resistant.

12 Claims, No Drawings

PERSONAL CARE PRODUCTS

CROSS-REFERENCE TO RELATED U.S. PATENTS

This application is a continuation-in-part of U.S. Ser. No. 10/233,838, filed Aug. 30, 2002, and assigned to the same assignee, and related to U.S. Pat. Nos. 5,869,695; 5,886,194; 5,959,122; 5,994,385; and 6,025,501, also assigned to the same assignee as herein.

BACKGROUND OF THE INVENTION

1. Field of the Invention

This invention relates to products useful in personal care formulations, and, particularly, to such products containing a mix of hair styling polymers and a compound or polymer having a carboxylic acid functionality which products possess the desirable physical attributes of toughness and cohesiveness, and a smooth feel, as well as high humidity curl retention, water-solubility and water-resistance.

2. Description of the Prior Art

Hair styling polymers which feel stiff on hair are rather brittle under a high applied stress; accordingly, these polymers shatter easily when strained appreciably. On the other hand, highly flexible polymers will bend under both high and low stress but they are generally considered by the user to be too soft for desirable hair styling.

In the aforementioned co-pending patent application, polymers are provided which have the desirable attributes of stiffness and flexibility, and have a strong affinity for hair imparting a natural feel for the user, and are also water-soluble and water-resistant. These natural feel polymers can be easily removed from a substrate such as hair or skin, or a textile fiber, by simple washing.

Accordingly, it is an object of this invention to provide improved personal care products containing polymers which exhibit toughness and cohesiveness.

Another object is to provide hair care products made by mixing such polymers with a compound or polymer having a carboxylic acid functionality, which gives a desired property such as excellent high humidity curl retention properties, water solubility and water-resistance.

These and other objects and features of the invention will be made apparent from the following description thereof.

SUMMARY OF THE INVENTION

The personal care products herein are made by mixing (A), which are polymers having defined amounts of repeat units of (a) a monomer (e.g. α-olefin)-maleic anhydride alkyl half-ester or full acid, (b) maleamic acid, and (c) a maleimide, as shown below:

(A)

(a) half-ester or full acid (b) maleamic acid (c) maleimide where:

$R$, $R_1$, $R_2$ and $R_3$ are selected from H, alkyl, alkoxy, cycloalkyl, aryl, ester, acid, hydroxy, hydroxyalkyl, amido, fluoro, halo and silyl, and $R_4$ is H or alkyl; and R' is a derivatizing group selected from X, a hydrophobic amine; Y, a hydrophilic amine; and Z, a polyether amine; and suitable mixtures thereof;

x, y and z are present, in mole %, of 0–99.9, 0–50 and 0.1–100, respectively; preferably 0–50, 0–5 and 50–100; and X, Y and Z preferably are present in mole ratios of 0–50:0–100:0–20; most preferably, 0–10:40–98:1–10, (B) and a compound or polymer with a carboxylic acid functionality.

DETAILED DESCRIPTION OF THE INVENTION

The (A) polymer component of the personal care product made herein is particularly characterized by repeat units which contain an abundance (by weight) of an amine derivatizing group which can hydrogen-bond with itself or other repeat units in the polymer to form an intra- or inter-molecular bonds in the polymer resulting in a pseudo-network polymer. This polymer thus acts as if it is crosslinked. Cohesion between such hydrogen-bonded molecules provides the polymer with water-resistance, but also with water solubility because, once the polymer is flooded with water, it will admit sufficient amount of water for solubilization. These polymers show good adhesion to natural substrates but can be removed easily if desired. Some amine derivatizers may also crystallize upon dry-down, resulting in enhanced water resistance.

Representative structural components of the (A) polymers of the invention are given below.

Polymer Backbone

Monomer-Maleic Anhydride Copolymer

Alkyl vinyl ether-maleic anhydride copolymer, e.g. methyl vinyl ether-maleic anhydride copolymer, or isobutyl vinyl ether-maleic anhydride copolymer; and derivatives thereof, including alpha-olefin-maleic anhydride copolymer, e.g. ethylene-maleic anhydride copolymer, or isobutylene-maleic anhydride copolymer; styrene-maleic anhydride copolymer, etc.

Derivatizers

Hydrophobic Amine (X)

Monofunctional α-unsubstituted primary or secondary monoamines, unsubstituted or substituted with alkyl, aryl, heterocyclic, aromatic, fluoro, silyl amino, carboxy and halogen; e.g. $C_1$–$C_{40}$ alkyl $NH_2$; butylamine, isobutyl amine, and octadecylamine. These amines may be included in the polymer to alter the solubility of the polymer.

Hydrophilic Amine (Y)

Hydroxy α-unsubstituted amines e.g. ethanolamine, isopropylamine, n-propanolamine, 3-amino-1-propanol; methoxyethyl amine, and diglycol amine; and alkyl diamines, e.g. 3-(dimethylamino)propylamine, dimethylethylene diamine, N-aminopropyl pyrrolidone, N-aminoethyl pyrrolidone, and 1-(3-aminopropyl)imidazole. These amines are included in the polymer to modify the adhesive/cohesive balance in the polymer, and to increase compatibility with other components in system.

Polyether Amine (Z)

Polyoxyalkylene amine, having the formula:

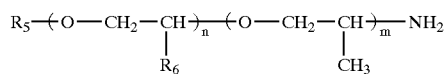

where $R_5$ and $R_6$ are selected from H and alkyl; e.g. $R_5$ is $CH_3$ and $R_6$ is H; and $R_5$ is $CH_3$ and $R_6$ is $CH_3$; and n and m are integers from 1–50; e.g. n=32 and m=10. These amines are obtainable as Jeffamine® M Monoamines (Huntsman Corp), with various molecular weights and ethylene oxide (EO)/propylene oxide (PO) ratios. These amines are present to provide natural feel properties in the polymer, i.e. softness and flexibility, as well as adhesive/cohesive balance.

The personal care products herein are made by mixing (A) with (B), a compound or polymer having a carboxylic acid functionality. Carboxylic acid functionality includes the free acid and the neutralized acid. A particularly preferred (B) polymer is a linear or crosslinked acrylic acid polymer, e.g. Carbapol®, preferably which is neutralized before mixing with (A). The result of mixing (A) and (B) is a complexed, synergistic product particularly suitable for hair care application because it has high humidity curl retention, and has an increased solution viscosity, as compared to (A) or (B) alone. The viscosity of the product can be predetermined by the relative amounts of (a), (b) and (c) in polymer (A). For example, 100 mole % in the (c) repeat unit will provide an opaque product, while dilution of the polymer with more (a) repeat units will form a more desirable clear, and less viscous product, upon mixing with (B).

The polymers strongly interact and upon dry down result in films with increased toughness and cohesiveness than individual polymer systems.

When these synergistic systems are used in a personal care hair styling application the resultant formulations have improved high humidity and curl retention (HHCR) when compared to similar formulations containing the individual polymers alone.

The degree of complexation between (A) and (B) can be predetermined by adjusting the mole ratio of maleimide in (A) to the carboxylic units in (B). Complexation is strongest for products in which the maleimide:carboxylic mole ratio approaches 1:1.

However, complexation is not as pH sensitive as typical acid-base complexed systems, e.g. PVP and acrylic acid; in fact, complexation can occur at a neutral pH. Thus personal care formulations at or around a neutral pH still possess synergistic complexation complexation of (A) and (B), with its resultant desirable properties and physical attributes.

The invention will now be described with reference to the following examples.

EXAMPLE 1

Step 1

Preparation of Polymer (A)

The following were charged into a 2-liter, stainless steel high pressure reactor.

| | |
|---|---|
| P(maleic anhydride/isobutene) (Man) | 72.94 g |
| 3-(dimethylamino) propylamine (50 mol % based on Man) | 24.17 g |
| Jeffamine ® M-2070 (2 mol % based on Man) (M.W. 2,000, 70/30 EO/PO) (water soluble) | 20.73 g |
| Triethylamine (43 mol % based on Man) (Neutralizer) | 20.59 g |
| Methanol | 257.07 g |

The reactor was sealed, purged 3 times with $N_2$ gas, and heating was begun according to the following heating profile.

| | |
|---|---|
| Ambient | → 90° C., 1½ hr. |
| 90° C. | → 90° C., 2 hr. |
| 90° C. | → 130° C., 1½ hr. |
| 130° C. | → 130° C., 8 hr. |
| 130° C. | → 35° C., 1 hr. |

At the end of the heating cycle, the polymer product was obtained as a lightly viscous, yellow, clear solution; then it was flooded with water to give a viscous, hazy, yellow-colored solution.

Step 2

Mixing Polymer (A) with Carboxylic Acid Containing Polymer (B)

The polymer solution (A) was mixed with neutralized Carbopol®, a crosslinked acrylic acid polymer, in amounts of 2 and 0.5 wt. %, respectively, and in an amount present in a typical styling gel formulation. A thick gel having a viscosity greater than (A) or (B) was obtained after an hour. The gel formulation was applied to hair and the resultant film was stressed. The film showed a natural feel, combining firm and flexible characteristics, water-resistance and water-solubility, and excellent high humidity curl retention.

EXAMPLE 2

Step 1

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 | 42.35 g |
| (M.W. 2,000, 5/95 EO/PO (water-insoluble)) | |
| Jeffamine M-2070 | 42.35 g |
| (M.W. 2,000, 70/30 EO/PO (water-soluble)) | |
| Triethylamine | 31.30 g |
| Ethanol | 510.20 g |

The reactor was sealed and purged with an inert gas. The following heating profile was initiated:

| | |
|---|---|
| Heat to 125° C. | 4 hours |
| Hold at 125° C. | 12 hours |
| Cool to 35° C. | 1 hour |

After the heating profile was complete, the polymer solution was discharged from the reactor. The resultant material was a viscous, clear yellow solution. This material was laid down as a film and allowed to dry. A non-brittle film resulted which was water soluble. Exchanging ethanol for water gave a water-based polymer solution having similar properties to the ethanol-based material.

Step 2

This step was carried out as in Example 1 to provide similar results.

EXAMPLE 3

Step 1

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 | 84.70 g |
| Triethylamine | 31.30 g |
| Ethanol | 510.20 g |

The reactor was sealed and purged with an inert gas. The following heating profile was initiated:

| | |
|---|---|
| Heat to 125° C. | 4 hours |
| Hold at 125° C. | 12 hours |
| Cool to 35° C. | 1 hour |

After the heating profile was complete, the polymer solution was discharged from the reactor. The resultant product was a viscous, clear yellow solution. This material was laid down as a film and allowed to dry. A non-brittle film resulted. Exchanging with water gave a water-based polymer solution having similar properties to the ethanol-based material.

Step 2

This step was carried out as in Example 1 to provide similar results.

EXAMPLE 4

Step 1

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 | 84.70 g |
| Jeffamine M-2070 | 33.90 g |
| Triethylamine | 31.30 g |
| Ethanol | 573.17 g |

The reactor was sealed and purged with an inert gas. The following heating profile was initiated:

| | |
|---|---|
| Heat to 125° C. | 4 hours |
| Hold at 125° C. | 12 hours |
| Cool to 35° C. | 1 hour |

After the heating profile was complete, the polymer solution was discharged from the reactor. The resultant material was a viscous clear yellow solution. This material, when laid down as a film and allowed to dry, resulted in a flexible film. This same material can be exchanged with water to give a water-based polymer solution having similar properties to the ethanol-based material.

Step 2

This step was carried out as in Example 1 to provide similar results.

EXAMPLE 5

Step 1

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 | 101.70 g |
| Jeffamine M-2070 | 84.70 g |
| Triethylamine | 31.30 g |
| Ethanol | 699.08 g |

The reactor was sealed and purged with an inert gas. The following heating profile was initiated:

| | |
|---|---|
| Heat to 125° C. | 4 hours |
| Hold at 125° C. | 12 hours |
| Cool to 35° C. | 1 hour |

After the heating profile was complete, the polymer solution was discharged from the reactor. The resultant material was a viscous clear yellow solution. This material, when laid down as a film and allowed to dry, resulted in a very flexible film. This same material can be exchanged with water to give a water-based polymer solution having similar properties to the ethanol-based material.

Step 2

This step was carried out as in Example 1 to provide similar results.

The products of Examples 1–5 were formulated into typical hair care products designed for use in the modes of styling, mousse, gel and spray hair care products. These products performed well in practice giving the user the advantages of the natural feel polymers therein, particularly a firm and flexible characteristic, water-resistance and water-solubility, and excellent high humidity curl retention, and predetermined viscosity.

While the invention has been described with particular reference to certain embodiments thereof, it will be understood that changes and modifications may be made which are within the skill of the art. Accordingly, it is intended to be bound only by the following claims,

What is claimed is:

1. The product of mixing (A), a polymer characterized structurally by repeat units of (a) a monomer-maleic anhydride alkyl half-ester or full acid, (b) maleamic acid, and (c) maleimide, of the formulas:

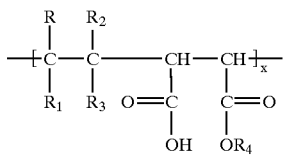

(a) half-ester or full acid

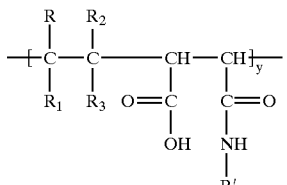

(b) maleamic acid

-continued

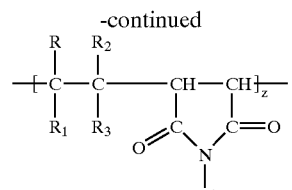

(c) maleimide where:
R, $R_1$, $R_2$ and $R_3$ are selected from H, alkyl, alkoxy, cycloalkyl, aryl, ester, acid, hydroxy, hydroxyalkyl, amido, fluoro, halo and silyl, and $R_4$ is H or alkyl; and R' is a polyoxyalkylene amine, having the formula:

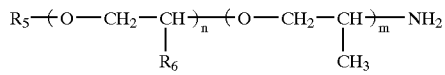

where $R_5$ and $R_6$ are selected from H and alkyl; and n and m are integers from 1–50; and
x, y and z are present, in mole %, of 0–99.9, 0–50 and 0.1–100, respectively;
and (B) a compound or polymer having a carboxylic acid functionality.

2. A product according to claim 1 wherein x=0–50, y=0–5 and z=5–100.

3. A product according to claim 1 wherein X, Y and Z are presenting a mole ratio of 0–10:40–98:1–10.

4. A product according to claim 1 wherein $R_5$ is $CH_3$ and $R_6$ is H.

5. A product according to claim 1 wherein both $R_5$ and $R_6$ are $CH_3$.

6. A product according to claim 1 wherein n=32 and m=10.

7. A product according to claim 1 wherein, in (a), said monomer is an α-olefin.

8. A product according to claim 1 wherein (B) is a crosslinked carboxylic acid containing polymer.

9. A product according to claim 8 wherein (B) is a crosslinked acrylic acid polymer.

10. A product according to claim 1 wherein (B) is a linear carboxylic acid containing polymer.

11. A product according to claim 1 wherein (B) is an acrylic acid containing polymer.

12. A product according to claim 1 wherein the mole ratio of maleimide in (A) to the carboxylic units in (B) is about 1:1.

* * * * *